（12）United States Patent
Barker et al.

(10) Patent No.: US 11,083,565 B2
(45) Date of Patent: Aug. 10, 2021

(54) SYSTEMS AND METHODS FOR CORNEAL TRANSPLANTS

(71) Applicant: CorneaGen Inc., Seattle, WA (US)

(72) Inventors: Jerry W. Barker, Gretna, VA (US); Douglas C. Drabble, Winston-Salem, NC (US); Matthew Giegengack, Winston-Salem, NC (US)

(73) Assignee: CORNEAGEN INC., Seattle, WA (US)

( * ) Notice: Subject to any disclaimer, the term of this patent is extended or adjusted under 35 U.S.C. 154(b) by 670 days.

(21) Appl. No.: 16/000,476

(22) Filed: Jun. 5, 2018

(65) Prior Publication Data

US 2018/0344450 A1    Dec. 6, 2018

Related U.S. Application Data

(60) Provisional application No. 62/515,528, filed on Jun. 5, 2017.

(51) Int. Cl.
*A61F 2/14* (2006.01)
*A61F 9/00* (2006.01)

(52) U.S. Cl.
CPC ............ *A61F 2/142* (2013.01); *A61F 2/145* (2013.01); *A61F 2/147* (2013.01); *A61F 2/1451* (2015.04); *A61F 2/1453* (2015.04); *A61F 9/0017* (2013.01)

(58) Field of Classification Search
CPC ........ A61F 2/142; A61F 2/145; A61F 2/1451; A61F 2/1453; A61F 2/147; A61F 9/0017
See application file for complete search history.

(56) References Cited

U.S. PATENT DOCUMENTS 5,755,785 A    5/1998  Rowsey et al.
5,824,086 A *  10/1998 Silvestrini ............ A61F 9/0017
                                                  623/5.11

(Continued)

FOREIGN PATENT DOCUMENTS

EP      2384722 A1      11/2011
WO   2009158723 A2     12/2009
WO   2018/039478 A1     3/2018

OTHER PUBLICATIONS

International Search Report for PCT/US2018/036059, dated Aug. 24, 2018.
Extended European Search Report dated Feb. 8, 2021, 5 pages.

*Primary Examiner* — William H Matthews
(74) *Attorney, Agent, or Firm* — Polsinelli PC; Michelle L. McMullen; Allison Krepel

(57) ABSTRACT

Corneal transplant procedures may involve suturing an implant of healthy corneal tissue to a recipient cornea. The sutures may cause unwanted deformation of the corneal implant and the recipient cornea. A supporting structure may be embedded into the corneal implant to enhance the stability of the corneal implant and the recipient cornea and to reduce the likelihood of unwanted deformation when the corneal implant is sutured to the recipient cornea. According to one embodiment, a corneal implant includes donor corneal tissue extracted from a donor cornea. The donor corneal tissue includes an interior channel formed at a depth below an anterior surface. The corneal implant includes a supporting structure formed from non-tissue material and positioned in the channel.

20 Claims, 2 Drawing Sheets

(56) References Cited

U.S. PATENT DOCUMENTS

| | | | |
|---|---|---|---|
| 6,197,019 B1* | 3/2001 | Peyman | A61F 2/147 |
| | | | 606/4 |
| 6,789,544 B2 | 9/2004 | Massimo et al. | |
| 8,388,608 B1 | 3/2013 | Agnieszka | |
| 2010/0198197 A1 | 8/2010 | Monteiro | |
| 2011/0281352 A1 | 11/2011 | Raeder et al. | |
| 2016/0331515 A1 | 11/2016 | Ben Nun et al. | |
| 2019/0192281 A1* | 6/2019 | Paschalls | A61F 2/142 |

\* cited by examiner

SYSTEMS AND METHODS FOR CORNEAL TRANSPLANTS

CROSS-REFERENCE TO RELATED APPLICATIONS

This application claims the benefit of, and priority to, U.S. Provisional Patent Application Ser. No. 62/515,528, filed Jun. 5, 2017, the contents of which are incorporated entirely herein by reference.

BACKGROUND

Field

The present disclosure pertains to systems and methods for treating disorders of the eye, and more particularly, to systems and methods for transplanting a cornea to treat such disorders.

Description of Related Art

Various disorders of the eye may result from diseased/damaged corneal tissue. The diseased/damaged corneal tissue can affect vision by scattering and/or distorting light and causing glare and/or blurred vision. In some cases, proper vision can only be restored by a corneal transplant which replaces the diseased/damaged corneal tissue with healthy tissue from an organ donor. For instance, treatment of keratoconus, a degenerative disorder that causes weakness and abnormal shaping of the cornea, may ultimately require corneal transplant surgery.

SUMMARY

Systems and methods of the present disclosure corneal employ corneal transplants to treat eyes with diseased/damaged corneal tissue. Corneal transplant procedures may involve suturing an implant of healthy corneal tissue to a recipient cornea. The sutures and other aspects of the transplant procedure, however, may cause unwanted deformation of the corneal implant and the recipient cornea. Such deformation may cause refractive errors. According to aspects of the present disclosure, a supporting structure may be embedded into the corneal implant to enhance the stability of the corneal implant and the recipient cornea and to reduce the likelihood of unwanted deformation when the corneal implant is sutured to the recipient cornea.

According to one embodiment, a corneal implant includes donor corneal tissue extracted from a donor cornea. The donor corneal tissue has an anterior surface and a posterior surface. The donor corneal tissue includes an interior channel formed at a depth below the anterior surface. The channel has a channel shape. The corneal implant includes a supporting structure formed from non-tissue material and is positioned in the channel. The supporting structure has a supporting-structure shape and provides support to resist deformation of the donor corneal tissue.

According to another embodiment, a method producing a corneal implant includes providing donor corneal tissue from a donor cornea. The donor corneal tissue has an anterior surface and a posterior surface. The method includes forming an interior channel in the corneal tissue at a depth below the anterior surface. The channel has a channel shape. The method includes positioning a supporting structure formed from non-tissue material in the channel of the donor corneal tissue. The supporting structure has a supporting-structure shape and provides support to resist deformation of the donor corneal tissue.

According to yet another embodiment, a method for transplanting a corneal implant includes providing a corneal implant. The corneal implant includes donor corneal tissue extracted from a donor cornea. The corneal tissue has an anterior surface and a posterior surface. The corneal tissue includes an interior channel formed in the donor corneal tissue at a depth below the anterior surface. The channel has a channel shape. The corneal implant includes a supporting structure formed from non-tissue material and positioned in the channel. The supporting structure has a supporting-structure shape and provides support to resist deformation of the donor corneal tissue. The method includes removing unwanted corneal tissue from a recipient cornea and correspondingly forming a cavity in the recipient cornea. The method includes positioning the corneal implant in the cavity. The method includes coupling, with sutures, the corneal implant to the recipient cornea.

DETAILED DESCRIPTION

Various disorders of the eye may result from diseased/damaged corneal tissue. The diseased/damaged corneal tissue can affect vision by scattering and/or distorting light and causing glare and/or blurred vision. In some cases, proper vision can only be restored by a corneal transplant which replaces the diseased/damaged corneal tissue with healthy tissue from an organ donor.

Figure 1A:
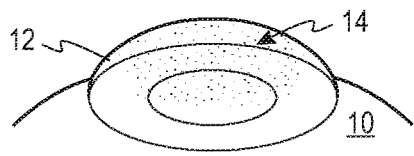
FIG. 1A illustrates a recipient eye with diseased/damaged corneal tissue.
Figure 1B:
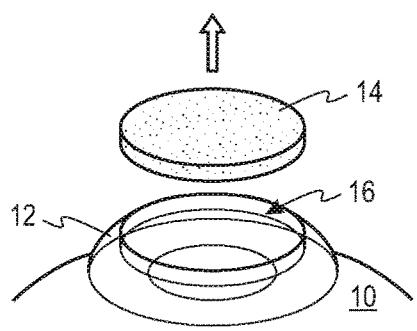
FIG. 1B illustrates removal of the diseased/damaged corneal tissue from the recipient eye of FIG. 1A.
Figure 1C:
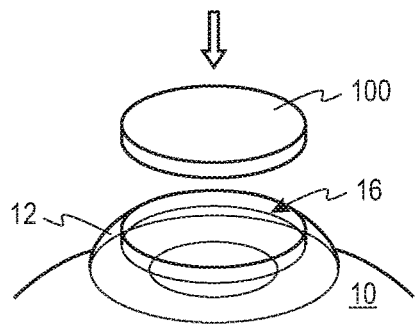
FIG. 1C illustrates positioning of a corneal implant relative to the recipient eye after the diseased/damaged corneal tissue is removed from the recipient eye as illustrated in FIG. 1B.
Figure 1D:
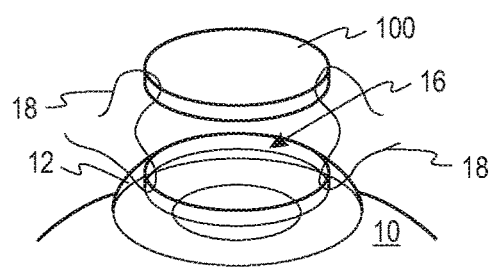
FIG. 1D illustrates suturing of the corneal implant in the recipient eye after the corneal implant is positioned relative to the recipient eye as illustrated in FIG. 1C.

FIGS. 1A-D illustrate perspective views of an example transplant procedure where a corneal implant 100 from a donor cornea is introduced into an eye 10. As shown in FIG. 1A, the eye 10 includes a cornea 12, which has diseased/damaged corneal tissue 14. Treatment of the eye 10 via corneal transplant involves surgical removal of the diseased/damaged corneal tissue 14 from the eye 10 as shown in FIG. 1B. The removal of the diseased/damaged corneal tissue 14 correspondingly produces a cavity 16 in the cornea 12. As FIG. 1C shows, the cavity 16 provides a bed in the cornea 12 for receiving the corneal implant 100. In some cases, the cavity 16 may be further shaped with a cutting instrument (e.g., a laser) to accommodate the size and shape of the corneal implant 100. Alternatively or additionally, the corneal implant 100 may be further shaped with a cutting instrument (e.g., a laser) to accommodate the size and shape of the cavity 16. As shown in FIG. 1D, the corneal implant 100 is received into the cavity 16 and coupled to the recipient cornea 12 with one or more sutures 18, e.g., fine nylon suture thread. Once the recipient cornea 12 has healed and fully accepts the corneal implant 100, the sutures 18 can be removed.

Figure 2A:
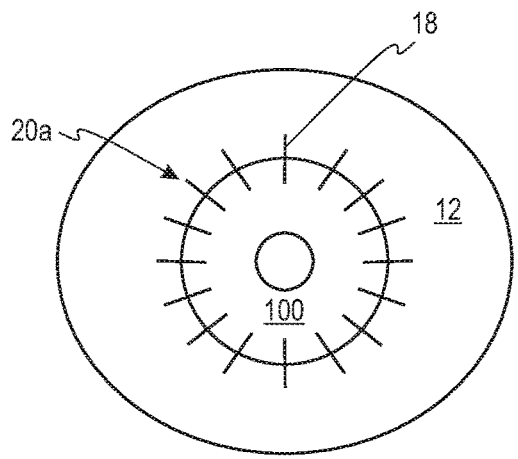
FIG. 2A illustrates an example suture pattern for a corneal transplant.
Figure 2B:
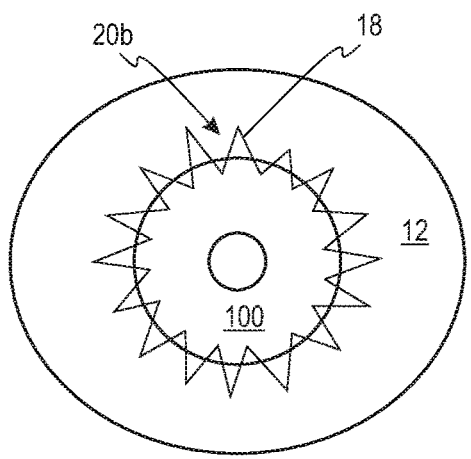
FIG. 2B illustrates another example suture pattern for a corneal transplant.

FIGS. 2A-B illustrate respective top views of example patterns 20a, b of sutures 18 that keep the corneal implant 100 in place for the transplant. Other implementations, however, are not limited to the example suture patterns 20a, b shown in FIGS. 2A-B. In the example pattern 20a, a series of individual sutures 18 are arranged along the periphery of the corneal implant 100, where each individual suture 18 passes through the recipient cornea 12 and the corneal implant 100 to couple the corneal implant 100 to the recipient cornea 12. In the example pattern 20b, one or more sutures 18 each pass alternately through the recipient cornea 12 and the corneal implant 100 along the periphery of the corneal implant 100 and create a zig-zag pattern between the recipient cornea 12 and the corneal implant 100. If plurality of sutures 18 is employed, the sutures 18 may form a plurality of overlapping zig-zag patterns.

Because the recipient cornea 12 and the corneal implant 100 are bodies of soft tissue, the forces and/or torques applied by the sutures 18 may deform the shapes of the corneal implant 100 and the recipient cornea 12. In some cases, other aspects of the transplant procedure may also contribute to the deformations. Such deformations may result in aberrations or other abnormal shaping that affect vision by scattering and/or distorting light travelling through the recipient cornea 12. Patients may require contact lenses or glasses after corneal transplants to correct refractive errors caused by such deformations.

To reduce or minimize unwanted deformation of a corneal implant and the recipient cornea 12, a supporting structure may be embedded into the corneal implant so that the corneal implant can resist the forces and/or torques applied by the sutures 18 and can maintain its desired shape more effectively. Although the supporting structure is embedded in the corneal implant, the supporting structure can also support the structure of the recipient cornea 12. In general, the supporting structure enhances the stability of the corneal implant and the recipient cornea and reduces the likelihood of refractive errors after the corneal implant is transplanted into the recipient cornea 12.

Figure 3A:
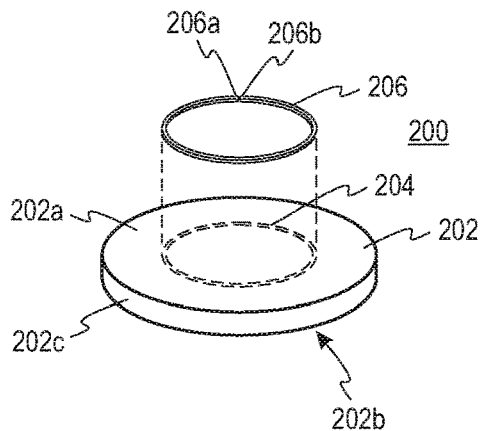
FIG. 3A illustrates an exploded view of an example corneal implant including donor corneal tissue and a supporting structure, according to aspects of the present disclosure.

FIG. 3A illustrates an exploded view of an example corneal implant 200. The corneal implant 200 includes corneal tissue 202 extracted from a donor cornea. The donor corneal tissue 202 may be sized and shaped with a cutting instrument (e.g., a laser) for transplant into a recipient cornea. The donor corneal tissue 202 has an anterior surface 202a and a posterior surface 202b. As shown in FIG. 3A, the donor corneal tissue 202 may have a substantially circular perimeter defined by an edge 202c extending between the anterior surface 202a and the posterior surface 202c. For instance, the substantially circular perimeter of the donor corneal tissue 202 may be approximately 8 mm in diameter. In other embodiments, however, the donor corneal tissue 202 may have a perimeter of another shape, e.g., ellipse, polygon, etc.

A narrow interior channel 204 (i.e., enclosed passageway) is formed in the donor corneal tissue 202 below the anterior surface 202a. According to one approach, a femtosecond laser can be focused at a depth below the anterior surface 202a to cut the channel 204 through the donor corneal tissue 202. The channel 204, for instance, may have a substantially annular shape, i.e., shaped as a thin ring, as shown in FIG. 3A. In addition, the channel 204 may be centered relative to the anterior surface 202a of the donor corneal tissue 202.

The corneal implant 200 also includes a supporting structure 206. The supporting structure 206 may be formed from non-tissue material. For instance, in some embodiments, the supporting structure 206 may be formed from a plastic. In other embodiments, the supporting structure 206 may be formed from a nickel titanium alloy, also known as Nitinol. Like the channel 204, the supporting structure 206 is substantially annular in shape, i.e., shaped as a thin ring. For instance, the supporting structure 206 may be approximately 3 mm in diameter. As shown in FIG. 3A, the supporting structure 206 may be defined by a narrow piece of material having two ends 206a, b, where the piece of material is curved so that the two ends 206a, b meet on a circle. As such, the annular shape of the supporting structure 206 has a small break between the two ends 206a, b.

Figure 3B:
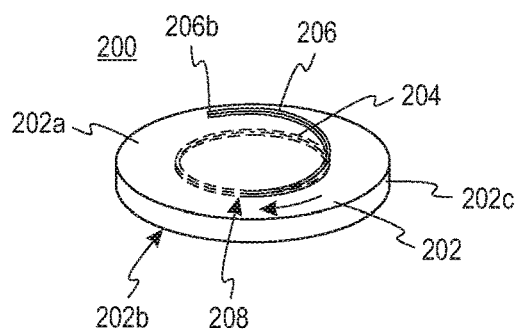
FIG. 3B illustrates an example approach for positioning the supporting structure in the donor corneal tissue of FIG. 3A, according to aspects of the present disclosure.

FIG. 3B illustrates an example approach for positioning the supporting structure 206 into the channel 204. A small incision 208 may be formed in the corneal tissue 202 to provide access to the channel 204 from the anterior surface 202a. The end 206a (or alternatively the end 206b) of the supporting structure 206 may be introduced into the small incision 208, and the supporting structure 206 may be guided (i.e., fed) through the small incision 208 and into the channel 204. The supporting structure 206 is sufficiently flexible to be manipulated in the manner shown in FIG. 3B.

Figure 3C:
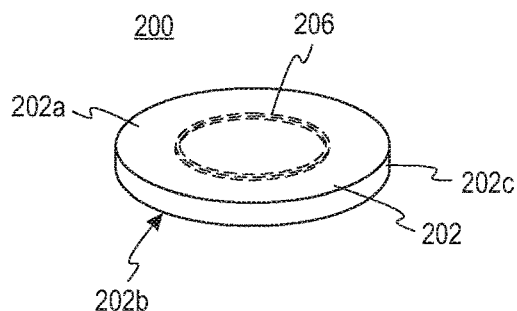
FIG. 3C illustrates an assembled view of the example corneal implant of FIG. 3A, according to aspects of the present disclosure.

FIG. 3C illustrates an assembled view of the example corneal implant 200. In particular, the supporting structure 206 is positioned in the channel 204. Formed from plastic, nickel titanium alloy, etc., the supporting structure 206 provides sufficient rigidity to support the donor corneal tissue 202 and to resist deformation of the donor corneal tissue 202. In general, the supporting structure 206 is more rigid than the donor corneal tissue 202, but provides sufficient flexibility for use in the eye 10.

As described above, the channel 204 and the supporting structure 206 have corresponding annular shapes so that the supporting structure 206 can be positioned in the channel 204. In some implementations, however, the channel 204 may have a smaller diameter than the supporting structure 206. For instance, if the supporting structure 206 is 3 mm in diameter, the channel 204 may be slightly less than 3 mm in diameter. As such, when the supporting structure 206 is received by the channel 204, the supporting structure 206 pushes against the tissue around the channel 204, which may expand outwardly. Correspondingly, the donor corneal tissue 202 around the channel 204 applies an inward pressure on the supporting structure 206 to hold the supporting structure 206 more securely in the channel 204.

Although the channel 204 and the supporting structure 206 shown in FIGS. 3A-C may have substantially annular shapes, other implementations may employ other shapes, such as an ellipse. In addition, although the supporting structure 206 shown in FIGS. 3A-C may be a single annular structure, the supporting structure 206 may be alternatively defined by a combination of a plurality of sub-structures. For instance, the supporting structure 206 may be defined by a combination of two half-circle structures that can be received into the channel 204 in a manner similar to a single annular structure. Furthermore, although FIGS. 3A-C may illustrate the example corneal implant 200 with one supporting structure 206 positioned in one corresponding channel 204, other embodiments may include more than one channel 204 receiving one or more respective supporting structures. For instance, an embodiment may include more than one channel 204 arranged concentrically to receive a respective annular supporting structure 206. The additional supporting structures 206 may provide additional stability and resistance to deformation of the donor corneal tissue 202.

Figure 4A:
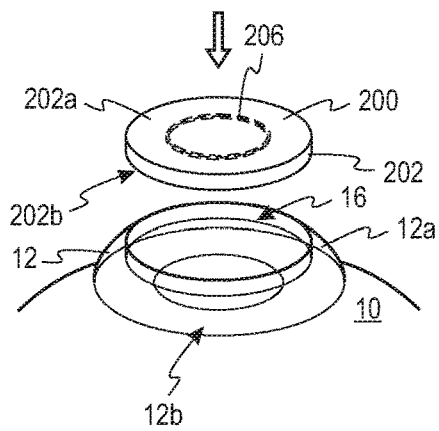
FIG. 4A illustrates positioning of an example corneal implant relative to a recipient eye after the diseased/damaged corneal tissue is removed from the recipient eye, according to aspects of the present disclosure.

As described above with reference to FIGS. 1A-B, a corneal transplant involves removing diseased/damaged corneal tissue 14 from the eye 10 and correspondingly forming a cavity 16 in the eye 10. Instead of the corneal implant 100, however, the corneal implant 200 may be implanted into the eye 10, where the supporting structure provides greater stability for the corneal implant 200 and the recipient cornea 12. As shown in FIG. 4A, the cavity 16 also provides a bed for receiving the corneal implant 200. In some cases, the cavity 16 may be further shaped with a cutting instrument (e.g., a laser) to accommodate the size and shape of the corneal implant 100. Alternatively or additionally, the corneal implant 100 may be further shaped a cutting instrument (e.g., a laser) to accommodate the size and shape of the cavity 16.

Figure 4B:
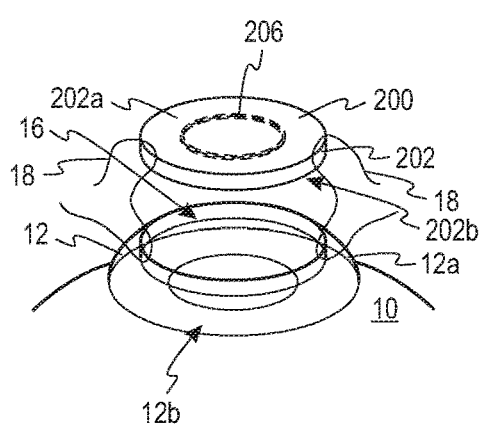
FIG. 4B illustrates suturing of the example corneal implant in the recipient eye after the corneal implant is positioned relative to the recipient eye as illustrated in FIG. 4A, according to aspects of the present disclosure.

As shown further in FIG. 4B, the corneal implant 100 is positioned in the cavity 16 and sutured in place with one or more sutures 18. When received in the cavity 16, the anterior surface 202a of the donor corneal tissue 202 is aligned with the anterior surface 12a (outwardly facing surface) of the recipient cornea 12 and the posterior surface 202b of the donor corneal tissue 202 is aligned with the posterior portion 12b (interior portion) of the recipient cornea 12.

As described above, the donor corneal tissue 202 and thus the corneal implant 200 may have a diameter of approximately 8 mm and the supporting structure 206 may have a diameter of approximately 3 mm. The supporting structure 206 may be positioned in the channel 204 which may be centered relative to the anterior surface 202a of the donor corneal tissue 202. When received in the cavity 16, the corneal implant 200 may be centered on the recipient cornea 12, which may for instance be approximately 12 mm in diameter. Accordingly, the supporting structure 206 of approximately 3 mm may be centered on the recipient cornea 12. In this case, the supporting structure 206 provides structural support and stability particularly for the central region of approximately 3 mm which is more critical for vision.

As described above, the one or more sutures 18 may apply forces and/or torques that can deform the shapes of the corneal implant 100 and the recipient cornea 12. The supporting structure 206, however, supports the structures of the corneal implant 100 and the recipient cornea 12 to reduce or minimize the deformation caused by such forces and/or torques. In general, the supporting structure 206 enhances the stability of the corneal implant 200 and the recipient cornea 12 and reduces the likelihood of refractive errors after the transplant procedure.

Once the recipient cornea 12 has healed and fully accepts the corneal implant 200, the sutures 18 can be removed. In some cases, the supporting structure 206 may also be removed after sutures 18 have been removed.

In some embodiments, the supporting structure 206 may be translucent (e.g., a translucent plastic) so that it does not interfere with the light entering the cornea 10 and affect the patient's vision. In other embodiments, the supporting structure 206 may be opaque and light-absorbing (e.g., dark in color), so that light entering the cornea 10 is not reflected by the supporting structure 206 to create halos or other glare in the patient's vision.

In addition to supporting the shape of the donor corneal tissue 202 and the recipient cornea 12, the supporting structure 206 may be configured to modify the refractive profile of the donor corneal tissue 202. In other words, the donor corneal tissue 202 defines a refractive profile, and in response to receiving the supporting structure 206 into the channel 204, the supporting structure 206 modifies the refractive profile of the donor corneal tissue 202 to provide a desired refractive correction for the recipient cornea 10. For instance, the supporting structure 206 may be configured to address myopia, hyperopia, and/or astigmatism in the recipient cornea 12.

Furthermore, the supporting structure 206 may also be configured to apply medication or other drug to the donor corneal tissue 202 and/or the recipient cornea 12. In some implementations, such medication may promote healing of the recipient cornea and/or prevent infection. In other implementations, such medication may reduce the likelihood of rejection of the corneal implant 200. For instance, the invasion of new blood vessels into the cornea, also known as corneal neovascularization, allows host immune effector lymphocytes to access donor antigens more easily and may increase the likelihood of rejection of implants from donor cornea. As such, the supporting structure 206 may carry a medication for treating corneal neovascularization.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

We claim:

1. A corneal implant, comprising:
    donor corneal tissue extracted from a donor cornea, the donor corneal tissue having an anterior surface and a posterior surface, the donor corneal tissue including an interior channel formed at a depth below the anterior surface, the channel having a channel shape; and
    a supporting structure formed from non-tissue material and positioned in the channel, the supporting structure having a supporting-structure shape and providing support to resist deformation of the corneal tissue.

2. The corneal implant of claim 1, wherein the donor corneal tissue has a substantially circular perimeter defined by an edge extending between the anterior surface and the posterior surface.

3. The corneal implant of claim 2, wherein the substantially circular perimeter of the donor corneal tissue is approximately 8 mm in diameter.

4. The corneal implant of claim 1, wherein the channel shape and the supporting-structure shape are substantially annular.

5. The corneal implant of claim 4, wherein the supporting structure is approximately 3 mm in diameter.

6. The corneal implant of claim 4, wherein the channel shape has a smaller diameter than the supporting-structure shape.

7. The corneal implant of claim 1, wherein in response to receiving the supporting structure into the channel, the donor corneal tissue applies an inward pressure on the supporting structure to hold the supporting structure securely in the channel.

8. The corneal implant of claim 1, wherein the supporting structure is defined by a combination of a plurality of sub-structures.

9. The corneal implant of claim 1, wherein the supporting structure is formed from a plastic.

10. The corneal implant of claim 1, wherein the supporting structure is formed from a nickel titanium alloy.

11. The corneal implant of claim 1, wherein the supporting structure is formed from a translucent material.

12. The corneal implant of claim 1, wherein the supporting structure is formed from an opaque, light-absorbing material.

13. The corneal implant of claim 1, wherein the donor corneal tissue defines a refractive profile, and in response to receiving the supporting structure into the channel, the supporting structure modifies the refractive profile of the donor corneal tissue to provide a desired refractive correction for a cornea receiving the corneal implant.

14. The corneal implant of claim 1, further comprising a drug applied to the supporting structure.

15. A method for producing a corneal implant, comprising:

providing donor corneal tissue extracted from a donor cornea, the donor corneal tissue having an anterior surface and a posterior surface;

forming an interior channel in the donor corneal tissue at a depth below the anterior surface, the channel having a channel shape; and positioning a supporting structure formed from non-tissue material in the channel of the donor corneal tissue, the supporting structure having a supporting-structure shape and providing support to resist deformation of the donor corneal tissue.

16. The method of claim 15, further comprising cutting the donor corneal tissue to have an edge extending between the anterior surface and the posterior surface, the edge defining a substantially circular perimeter for the donor corneal tissue.

17. The method of claim 15, wherein the channel shape and the supporting-structure shape are substantially annular.

18. The method of claim 16, wherein the channel shape has a smaller diameter than the supporting-structure shape.

19. The method of claim 15, wherein the supporting structure is formed from a piece of material having two ends, and positioning the supporting structure in the channel of the donor corneal tissue includes:

forming an incision to provide access to the channel from the anterior surface of the donor corneal tissue;

introducing one end of the supporting structure through the incision; and guiding the supporting structure through the incision and into the channel.

20. The method of claim 15, wherein the donor corneal tissue defines a refractive profile, and in response to receiving the supporting structure into the channel, the supporting structure modifies the refractive profile of the donor corneal tissue to provide a desired refractive correction for a cornea receiving the corneal implant.

* * * * *